United States Patent [19]

Mizuno et al.

[11] 4,320,119
[45] Mar. 16, 1982

[54] **EXTRACTS OF *MARSDENIA CUNDURANGO* REICHENBACH FIL**

[75] Inventors: Den-ichi Mizuno, Kamakura; Hiroshi Mitsuhashi, Sapporo; Shigeru Abe, Tokyo; Koji Hayashi, Sapporo, all of Japan

[73] Assignee: Kenyaky Yogyo Kabushiki Kaisha, Tokyo, Japan

[21] Appl. No.: 178,903

[22] Filed: Aug. 18, 1980

[30] Foreign Application Priority Data

Aug. 23, 1979 [JP] Japan .................................. 54/107366

[51] Int. Cl.³ ..................... A61K 31/705; A61K 31/78
[52] U.S. Cl. ..................................... 424/182; 424/195
[58] Field of Search ................................ 424/195, 182

[56] References Cited
U.S. PATENT DOCUMENTS 116,530 6/1871 Baker .................................. 424/195

OTHER PUBLICATIONS

Koji et al., Chemical Abstracts vol. 93:204968b (1980) citing Chem. Pharm. Bull. 1980,28 (6), pp. 1954–1958.
Remington, The Practice of Pharmacy, 3rd Ed. (1895) published by J. B. Lippincott Co., Phil., p. 950.
The Dispensatory of U.S.A., 24th Ed. (1947) published by J. B. Lippincott Co., Phil., pp. 1409 and 1410.

*Primary Examiner*—Donald B. Moyer
*Attorney, Agent, or Firm*—Browdy and Neimark

[57] ABSTRACT

New extracts of *Marsdenia cundurango* Reichenbach fil., processes for preparing them, antitumor agents comprising them, compositions containing them and methods of treating tumor with them are described herein in which the extracts consist essentially of the portion of *Marsdenia cundurango* Reichenbach fil. which is soluble in lower alcohols and in chlorinated hydrocarbons other than carbon tetrachloride and is insoluble in aliphatic hydrocarbons.

4 Claims, 8 Drawing Figures

EXTRACTS OF *MARSDENIA CUNDURANGO* REICHENBACH FIL

The present invention relates to extracts of *Marsdenia cundurango* Reichenbach fil., processes for preparing them, antitumor agents comprising them, compositions containing them and methods of treating tumor with them.

*Marsdenia cundurango* Reichenbach fil. belonging to the family Asclepiadaceae is a shrub of somewhat winding type growing naturally on and between mountains in the northwest of South America. Its bark is employed as an aromatic but bitter stomachic at the time of digestive disorder and/or anorexia, usually in the form of fluid extract (Commentary for the ninth Japanese Pharmacopeia).

The components of the bark of *Marsdenia cundurango* Reichenbach fil. include condurangogenin-A, condurangogenin-C and many other pregnane type compounds and their esters and glycosides, and the extraction, separation, structures and so on of them have been reported in, for example, the following documents. But, their details are still unclear in many points.

R. Tschesche et al., Tetrahedron, 21, p. 1777 (1965); 21, p. 1797 (1965); 23, p. 1461 (1967); and 24, p. 4359 (1968). M. Pailer et al., Monatshefte für Chemie, 106, p. 37 (1975); Hiroshi Mitsuhashi et al., Chem. Pharm. Bull., 16, p. 2522 (1968).

As a result of their study, the inventors of the present invention have found that certain extracts of *Marsdenia cundurango* Reichenbach fil. and certain elution fractions obtained by subjecting the extracts to high pressure liquid chromatography (hereunder referred to as HPLC) have antitumor activity. Thus, the present invention has been completed.

Hereunder, the present invention will be explained in detail.

In carrying out the present invention, the bark of *Marsdenia cundurango* Reichenbach fil. is preferred. This bark may be a commercially available one, but it is preferably one well dried and finely divided soon after its collection.

In view of the nature of the preparation of extracts, the order of the use of solvents also is not critical in carrying out the present invention, and it may be changed according to convenience. A preferred embodiment of the process of the present invention is as follows:

(First operation)

*Marsdenia cundurango* Reichenbach fil., for example, its bark, is finely divided and extracted with an organic solvent, and the extract is concentrated to dryness under reduced pressure. As the organic solvent, methanol, ethanol, isopropanol or any other lower alcohol may be employed, but methanol is preferred.

Here, prior to the extraction, *Marsdenia cundurango* Reichenbach fil. may be defatted with an aliphatic hydrocarbon such as pentane, hexane, heptane, ligroine or petroleum ether. This pre-treatment is preferably effected using hexane in an amount 4–7 times (v/w) that of *Marsdenia cundurango* Reichenbach fil.

In an embodiment of this extraction operation, the extraction is effected by allowing the starting material-solvent mixture to stand at room temperature for from several to several tens of hours. Then, the mixture is filtered to yeild a filtrate. The residue is subjected to the same extraction-filtration as the above repeatedly, and all the filtrates are combined and concentrated to dryness under reduced pressure to yield an extract.

The extraction is usually effected at normal temperatures, but may be effected while heating in order to shorten the extraction time. This extraction with heating is preferably carried out on a water bath at a water bath temperature of 35°–55° C. for 4–6 hours using a reflux condenser. It may be effected according to the percolation method.

The amount of the solvent used is 2–5 times (v/w) that of *Marsdenia cundurango* Reichenbach fil. The extraction residue is preferably subjected to extraction under the same conditions as the above three or more times using the solvent in an amount 0.4–0.8 times (v/v) that of the solvent first used.

The separation may be conducted by paper filtration, centrifugation or the like. Better results are obtained by conducting the separation by suction filtration using commercially available filtration aids, for example, Radiolite (Showa Chemical Industry Co., Ltd. in Japan), Celite (Wako Junyaku Industry Co., Ltd. in Japan), Fibra Cel (Johns Manville Co., Ltd. in U.S.), etc.

The reduction in pressure is conducted in a usual manner, for example, using an aspirator, vacuum pump or the like.

As the extraction vessel, one with a glass-lined or enameled inner surface or one made of stainless steel is employed.

(Second operation)

To the extract obtained by the first operation, there is added a chlorinated hydrocarbon other than carbon tetrachloride such as chloroform or dichloromethane, followed by vigorous shaking to remove the insoluble portion. The insoluble portion is subjected to the same operation as the above repeatedly. All the remaining solutions are combined and concentrated to dryness under reduced pressure directly or after suction filtration. The amount of the solvent used is 2–6 times (v/w) that of the extract obtained by the first operation. The respective residues are preferably subjected to the same operation four or five times, but using the solvent in an amount 0.2–0.4 times (v/v) that of the solvent first used.

The suction filtration may be carried out in the same manner as in the first operation.

(Third operation)

The extract obtained by the second operation is dissolved in a chlorinated hydrocarbon other than carbon tetrachloride, such as chloroform or dichloromethane, in the minimum amount necessary to dissolve the former completely. To the resulting solution, there is added an aliphatic hydrocarbon such as pentane, n-hexane or heptane in an amount two to four times (v/v) that of the former followed by well stirring and allowing to stand for from several to several tens of hours to collect the insoluble portion.

The insoluble portion is subjected to the same operation as the above repeatedly. This operation is preferably conducted two or three times, each time using the solvent in an amount 0.4–0.6 times (v/v) that of the solvent first used. The thus obtained insoluble portion is well dried at a temperature of 50° C. or less under reduced pressure and then crushed to yield a brown powder-like extract.

The collection of the insoluble portion may be made by decantation, suction filtration or centrifugation with advantage.

The thus obtained extracts of the present invention have the following characteristic aspects.

1. Properties:

(1) It is a brown powder, tastes bitter and gives out a cinnamic acid-like odor when a caustic soda solution is added thereto followed by heating.

(2) Solubility

Soluble in lower alcohols and in chlorinated hydrocarbons other than carbon tetrachloride.

Insoluble in aliphatic hydrocarbons.

2. U.V. spectra $\lambda_{max}$ = 280 nm (in methanol)

3. Mass spectra

Show a base peak of cinnamoyl cation at m/e=131 and an ion peak of acetyl cation at m/e=43.

Thus, the presence of cinnamic and acetic esters in the extracts is suggested.

4. Liquid chromatography (Conditions)

Filler: silica gel (Wako-gel LC-5H-totally porous crushed type, 5 μ, manufactured by Wako Junyaku Industry Co., Ltd. in Japan)

Column: i.d. × 1. = 4 mm × 200 mm

Eluant: a mixture of n-hexane/chloroform/methanol (volumetric ratio=7:2:1)

Flow rate: 1.5 ml/min.

Pressure: 30 kg/cm$^2$.

Detection: at U.V. 280 nm (0.64 AUFS)

Under the above conditions, 20 mg of each of the extracts of the present invention, dissolved in 10 ml of chloroform is subjected to liquid chromatography. As is shown in the chromatograms depicted in FIGS. 1-8 of the accompanying drawings, the extracts of the present invention are mixtures consisting mainly of six components showing characteristic peaks in the chromatograms.

In the accompanying drawings.

5. Color reaction

Figure 1:
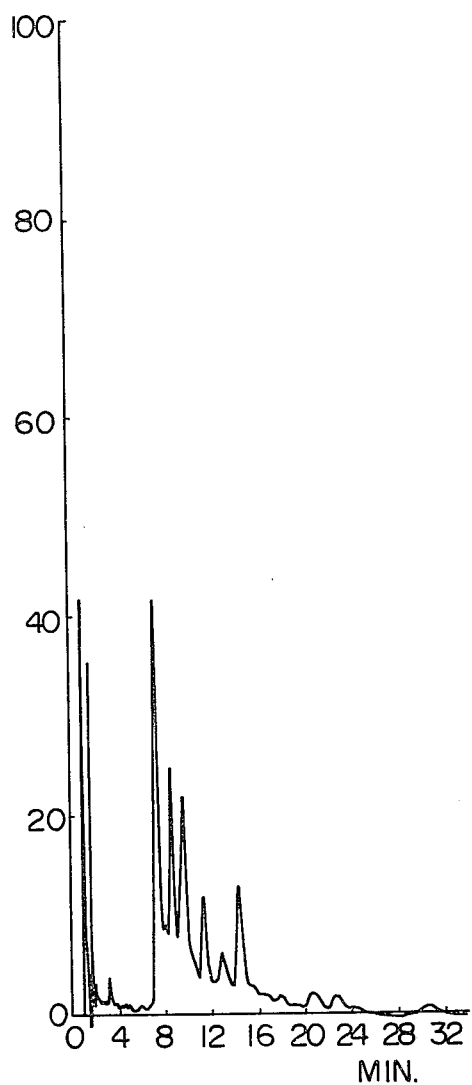
FIG. 1 shows a chromatogram obtained by subjecting the extract of Example 1 to analytical HPLC.

Keller Kiliani reaction [Helvetica Chimica Acta., 31, p. 883 (1948)]: positive (greenish brown)

Liebermann Burchard reaction [Iwanami's Dictionary of Physics and Chemistry, 3rd edition, p. 1411 (1977)]: positive (blueish green)

Thus, the extracts are supposed to consist mainly of steroid glycosides having 2,6-deoxysugars.

The antitumor activity of the extracts of the present invention was confirmed by the screening test mentioned below.

Two type tumors, Sarcoma-180 and *Ehrlich carcinoma*, were employed in the evaluation of the antitumor properties, and the tested tumors were of subcutaneous tubercle type.

The group to which the extracts of the present invention were administered consisted of seven mice while the control group consisted of ten mice.

Test method (1) Sarcoma-180

The experimental animals were six week old ICR male mice (body weight: 30-32 g).

The tumors were transplanted intraperitoneally into the mice. On the seventh day after the transplantation, the well grown cells of the tumors were taken out, and 4×10$^6$ cells of them were transplanted subcutaneously into the inguinal region of the mice to form solid tumors. At and after 24 hours after the transplantation, the extracts of the present invention dissolved in physiological saline solutions were administered to the mice intraperitoneally.

The volume of the respective solutions administered was 0.2 ml per mouse at one time, and the administration was conducted for ten days at a rate of one time per day. Only physiological saline solutions were given to the mice of the control group.

On the thirtieth day after the transplantation, the tumors were taken out to measure the average weight of the tumors of the mice of the group to which the extracts of the present invention had been administered (T) and that of the control group (C) to calculate the T/C (%).

(2) *Ehrlich carcinoma*

The experimental animals were six week old ddY male mice (body weight: 28-30 g).

The tumors were transplanted intraperitoneally into the mice. On the seventh day after the transplantation, the well grown cells of the tumors were taken out, and 1.5×10$^6$ cells thereof were transplanted subcutaneously into the inguinal region of the mice to form solid tumors, and then worked up as in the case of the Sarcoma-180 to calculate the T/C(%).

| Extract | Dose (mg/kg × times) | Results T/C (%) Ehrlich carcinoma | Sarcoma-180 |
|---|---|---|---|
| Extr. of Ex. 1 | 40 × 10 | 34.1 | 15.2 |
| Extr. of Ex. 2 | " | 29.3 | 25.7 |
| Extr. of Ex. 3 | " | 39.0 | 23.5 |
| Extr. of Ex. 4 | " | 32.3 | 35.2 |
| Extr. of Ex. 5 | " | 44.7 | 31.0 |
| Extr. of Ex. 6 | " | 40.1 | 39.3 |
| Extr. of Ex. 7 | " | 38.5 | 41.3 |
| Extr. of Ex. 8 | " | 33.0 | 30.0 |

Next, the extracts of the present invention were administered to five week old ddY male mice (body weight: 21-25 g) intraperitoneally to determine the acute toxic values (LD$_{50}$).

| Extract | Results LD$_{50}$ (mg/kg) |
|---|---|
| Extr. of Ex. 1 | 400 |
| Extr. of Ex. 2 | 415 |
| Extr. of Ex. 3 | 406 |
| Extr. of Ex. 4 | 417 |
| Extr. of Ex. 5 | 410 |

-continued

| Extract | Results LD$_{50}$ (mg/kg) |
| --- | --- |
| Extr. of Ex. 6 | 400 |
| Extr. of Ex. 7 | 390 |
| Extr. of Ex. 8 | 398 |

The extracts of the present invention may be administered to human body orally, by injection (subcutaneously or intramuscularly) or in any other manner.

When the extracts of the present invention are employed in the form of solid preparations for oral administration, the preparations may be tablets, granules, powders, capsules or the like. The preparations may contain additives, for example, an excipient such as a saccharide or cellulose preparation, a binder such as starch paste or methyl cellulose, a filler, a disintegrator and the like, all being ones usually used in the manufacture of medical preparations. In case the extracts of the present invention are employed as oral liquid preparations, they may be of any form selected from aqueous preparations for internal use, suspensions, emulsions, syrups, etc., and further they may be in the form of dried products which are dissolved prior to the use.

When the extracts of the present invention are orally administered to adults, they may be employed in a dose of 3.0–30.0 mg/kg per day. Here, of course, the dose may be increased or decreased appropriately depending on the conditions of disease, the age of the patient, the form of the preparation, etc.

The extracts of the present invention may be injected in the form of aqueous solutions, suspensions or oily or aqueous emulsions, but usually the injections are prepared by dissolving or suspending them in aqueous liquid media such as sterile water or physiological saline solutions. If necessary, conventionally used dissolving agents, stabilizers, preservatives, additives for preparing isotonic solutions, etc. may be added to the injections.

The thus obtained injection preparations are administered intramuscularly, subcutaneously or in any other appropriate manner. When the injections are administered to adults parenterally, they may contain 1.0–10.0 mg/kg of the extract of the present invention per day. Of course, this dose level is increased or decreased appropriately depending on the conditions of disease, the age of the patient, the form of the preparation administered, the administration manner and so on.

Hereunder, the present invention will be explained in detail with reference to examples given below.

EXAMPLE 1

One liter of methanol was added to 500 g of finely divided bark of *Marsdenia cundurango* Reichenbach fil., and the mixture was allowed to stand at room temperature overnight. Then the mixture was filtered, and the residue was further treated three times in the same manner as the above, each time using 0.75 l of methanol.

All the filtrates were combined, and then concentrated to dryness at 45° C. under reduced pressure to yield 69 g of an extract. To this extract transferred into a separatory funnel, there was added 150 ml of chloroform followed by vigorous shaking, and then the chloroform layer was obtained. To the residue, there was added 50 ml of chloroform to repeat the same operation as the above three times. All the chloroform extracts were combined and then subjected to suction filtration using Fibra Cel BH-40 (Johns Manville Co., Ltd.) as the filtration aid. The resulting filtrate was concentrated to dryness at 40° C. under reduced pressure to yield 42 g of an extract. This extract was dissolved in 50 ml of chloroform added thereto followed by the addition of 100 ml of n-hexane. The resulting mixture was well stirred and allowed to stand for 12 hours. Then, it was subjected to decantation to obtain the insoluble portion. This portion was dissolved in 25 ml of chloroform followed by the addition of 50 ml of n-hexane, and the solution was well stirred and allowed to stand for 2 hours. The solution was subjected to decantation to obtain the insoluble portion and then treated in the same manner as in the above three times. The finally obtained insoluble portion was dried at 45° C. under reduced pressure for 6 hours and crushed to yield 18 g of a brown powder-like extract.

The thus prepared 20 mg of the extract was dissolved in 10 ml of chloroform, and the resulting solution was subjected to analytical HPLC [filler: silica gel (Wako-gel LC-5H, manufactured by Wako Junyaku Industry Co., Ltd., totally porous crushed type, 5 $\mu$); column: i.d.×1.=4 mm×200 mm; eluant: a mixture of n-hexane/chloroform/methanol (volumetric ratio =7:2:1); flow rate: 1.5 ml/min.; pressure: 30 kg/cm$^2$; and detection: at U.V. 280 nm (0.64 AUFS)]. The obtained data is shown in the chromatogram depicted in FIG. 1 of the accompanying drawings.

EXAMPLE 2

In the same manner as the first operation in Example 1, 500 g of finely divided bark of *Marsdenia cundurango* Reichenbach fil. was extracted with chloroform.

Figure 2:
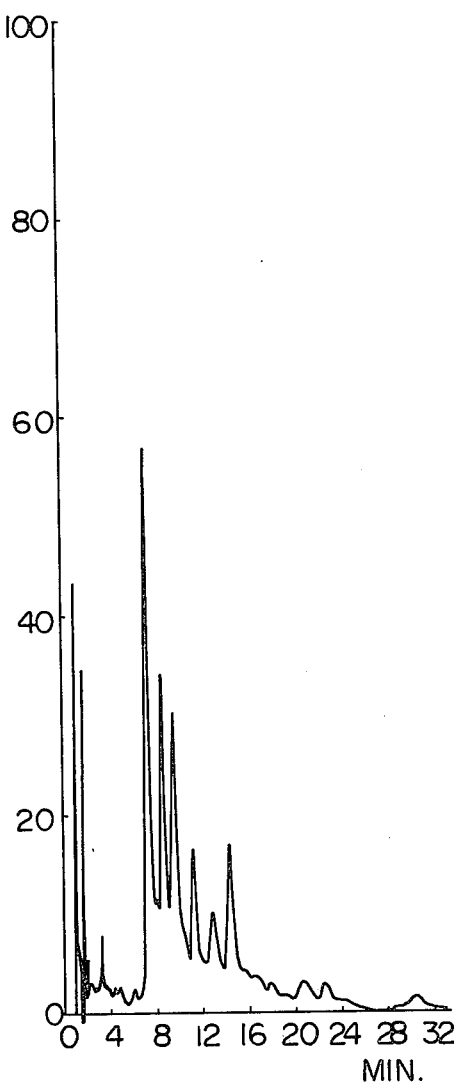
FIG. 2 shows a chromatogram obtained by subjecting the extract of Example 2 to analytical HPLC.

All the filtrates were combined and concentrated to dryness at 40° C. under reduced pressure to yield 46 g of an extract. To this extract, there was added 100 ml of methanol, and the mixture was well stirred and then filtered. The residue with 30 ml of methanol added thereto was treated in the same manner as the above four times. All the filtrates were combined and concentrated to dryness at 45° C. under reduced pressure to yield 24 g of an extract. This extract was dissolved in 50 ml of chloroform added thereto, and then treated as in Example 1 to yield 13 g of a brown powder-like extract. The data obtained by subjecting this extract to HPLC under the same conditions as in Example 1 is shown in the chromatogram depicted in FIG. 2 of the accompanying drawings.

EXAMPLE 3

In the same manner as in Example 1, but using ethanol instead of the methanol in the first operation, there was produced 14.1 g of a brown powder-like extract.

Figure 3:
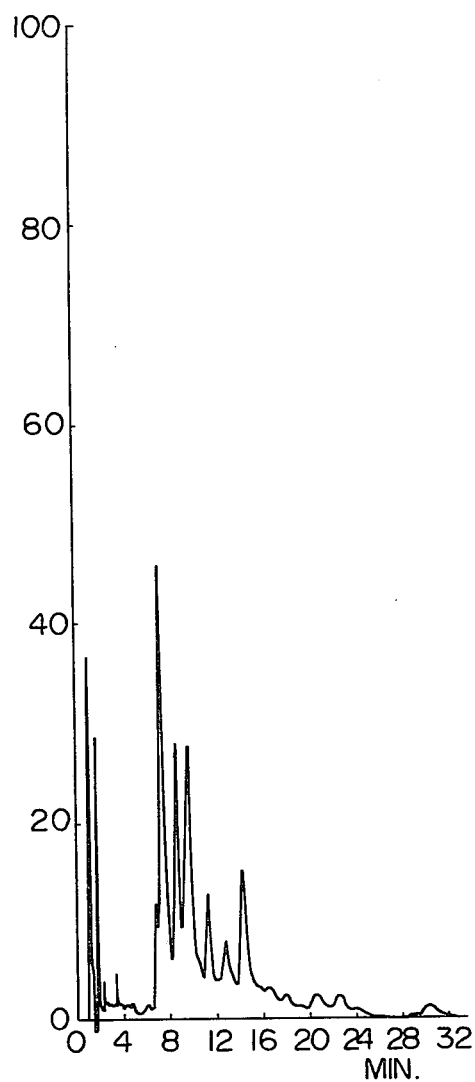
FIG. 3 shows a chromatogram obtained by subjecting the extract of Example 3 to analytical HPLC.

The data obtained by subjecting this extract to HPLC under the same conditions as in Example 1 is shown in the chromatogram depicted in FIG. 3 of the accompanying drawings.

EXAMPLE 4

In the same manner as in Example 1, but using isopropanol instead of the methanol in the first operation, there was produced 13.7 g of a brown powder-like extract.

Figure 4:
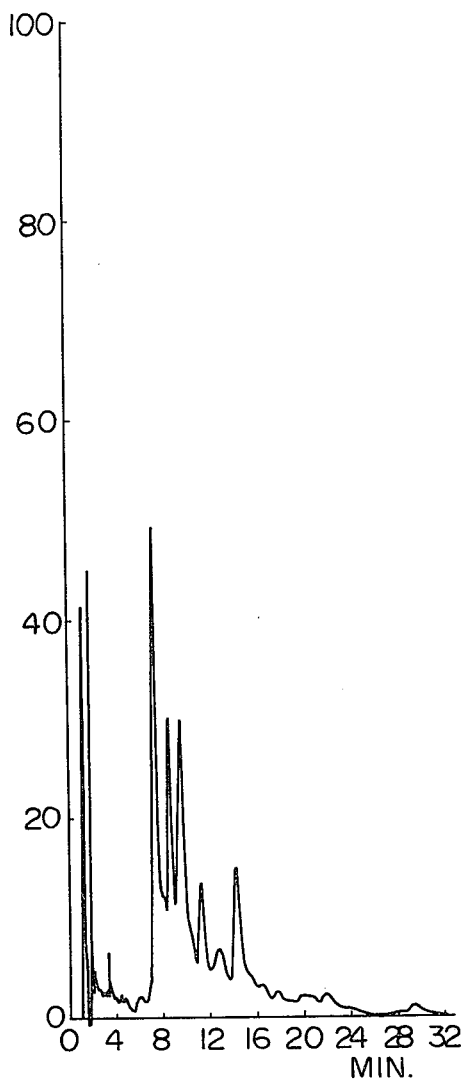
FIG. 4 shows a chromatogram obtained by subjecting the extract of Example 4 to analytical HPLC.

The data obtained by subjecting this extract to HPLC under the same conditions as in Example 1 is shown in the chromatogram depicted in FIG. 4 of the accompanying drawings.

EXAMPLE 5

In the same manner as in Example 1, but using dichloromethane instead of the chloroform in the second operation, there was produced 16 g of a brown powder-like extract.

Figure 5:
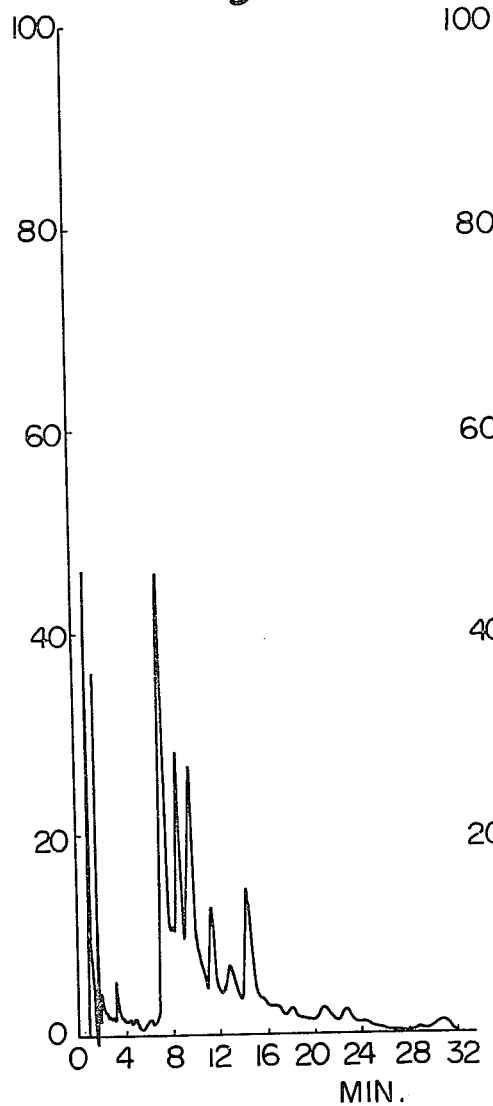
FIG. 5 shows a chromatogram obtained by subjecting the extract of Example 5 to analytical HPLC.

The data obtained by subjecting this extract to HPLC under the same conditions as in Example 1 is shown in the chromatogram depicted in FIG. 5 of the accompanying drawings.

EXAMPLE 6

In the same manner as in Example 1, but using pentane instead of the n-hexane in the third operation, there was produced 15.9 g of a brown powder-like extract.

Figure 6:
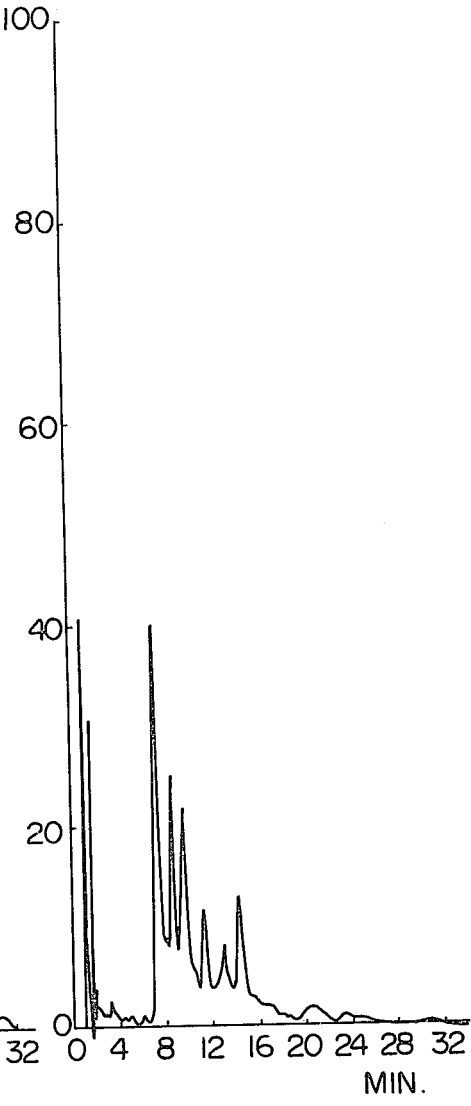
FIG. 6 shows a chromatogram obtained by subjecting the extract of Example 6 to analytical HPLC.

The data obtained by subjecting this extract to HPLC under the same conditions as in Example 1 is shown in the chromatogram depicted in FIG. 6 of the accompanying drawings.

EXAMPLE 7

In the same manner as in Example 1, but using heptane instead of the n-hexane in the third operation, there was produced 16.8 g of a brown powder-like extract.

Figure 7:
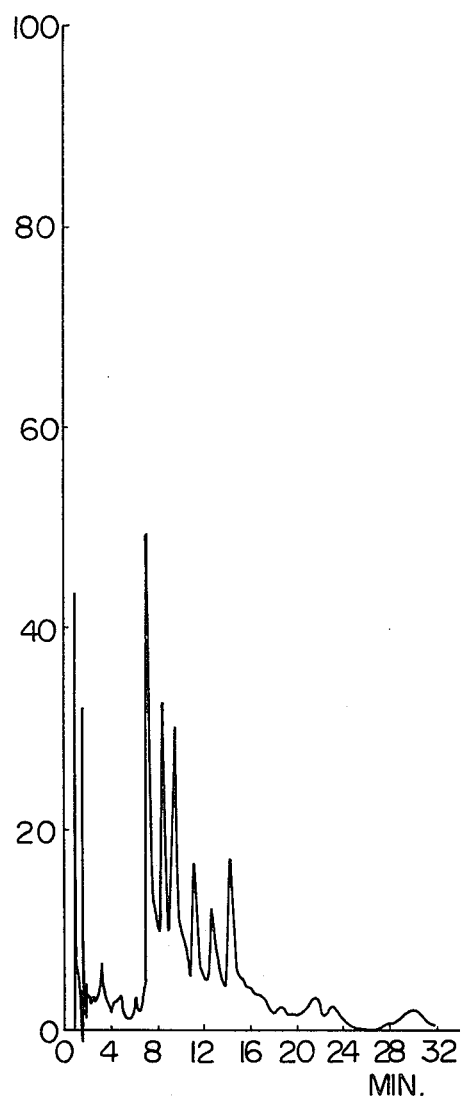
FIG. 7 shows a chromatogram obtained by subjecting the extract of Example 7 to analytical HPLC.

The data obtained by subjecting this extract to HPLC under the same conditions as in Example 1 is shown in the chromatogram depicted in FIG. 7 of the accompanying drawings.

EXAMPLE 8

To 500 g of finely divided bark of *Marsdenia cundurango* Reichenbach fil., there was added 1 liter of methanol, and the mixture was refluxed on a water bath at 50° C. using a reflux condenser for 5 hours for extraction. The filtration was conducted while hot, and the residue with 0.75 l of methanol added thereto was treated in the same manner as the above three times. Then, the mixture was worked up as in Example 1 to yield 21.5 g of a brown powder-like extract.

Figure 8:
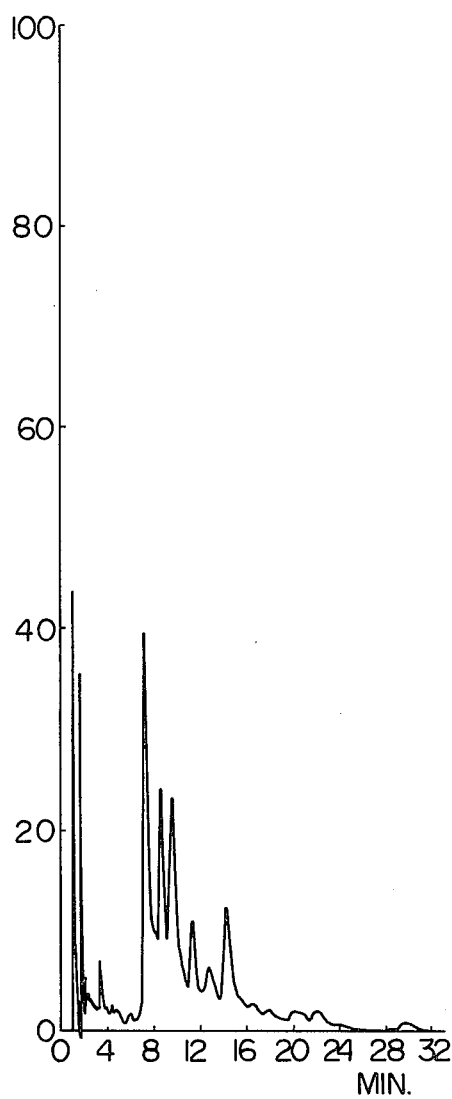
FIG. 8 shows a chromatogram obtained by subjecting the extract of Example 8 to analytical HPLC.

The data obtained by subjecting this extract to HPLC under the same conditions as in Example 1 is shown in the chromatogram depicted in FIG. 8 of the accompanying drawings.

What is claimed is:

1. An extract of *Marsdenia cundurango* Reichenbach fil. which is soluble in $C_{1-3}$ lower alcohols and in chloroform and dichloromethane and insoluble in pentane, hexane and heptane, and shows the chromatogram depicted in FIG. 1 of the accompanying drawings when subjected to analytical HPLC in which the filler is totally porous crushed type silica gel, 5 $\mu$; the column has an i.d. of 4 mm and a length of 200 mm; the eluant is a mixture of n-hexane/chloroform/methanol having a volumetric ratio of 7:2:1; the flow rate is 1.5 ml/min.; the pressure is 30 kg/cm$^2$; and detection is at U.V. 280 nm.

2. A process for preparing the extract as described in claim 1 comprising treating *Marsdenia cundurango* Reichenbach fil. with the following three types of solvents in an optional order:
    (1) a $C_{1-3}$ lower alcohol for collecting the portion which is soluble therein;
    (2) chloroform or dichloromethane for collecting the portion which is soluble therein; and
    (3) pentane, hexane or heptane for removing the portion which is soluble therein.

3. A pharmaceutical composition characterized by containing the extract of *Marsdenia cundurango* Reichenbach fil. as described in claim 1 in an amount effective against Sarcoma-180 and *Ehrlich carcinoma* tumors, and a pharmaceutically acceptable diluent or carrier.

4. A method of treating Sarcoma-180 or *Ehrlich carcinoma* in a living animal body comprising administering an effective amount of the extract as described in claim 1 to the body.

* * * * *

UNITED STATES PATENT AND TRADEMARK OFFICE
CERTIFICATE OF CORRECTION

PATENT NO. : 4,320,119
DATED : March 16, 1982
INVENTOR(S) : MIZUNO et al.

It is certified that error appears in the above—identified patent and that said Letters Patent are hereby corrected as shown below:

The assignee should read as follows:

[73] Assignee: Zenyaku Kogyo Kabushiki Kaisha, Tokyo, Japan

Signed and Sealed this

Thirteenth Day of March 1984

[SEAL]

Attest:

GERALD J. MOSSINGHOFF

Attesting Officer

Commissioner of Patents and Trademarks